United States Patent
Van den Heuvel

(10) Patent No.: US 10,238,871 B2
(45) Date of Patent: Mar. 26, 2019

(54) IMPLANTABLE MEDICAL DEVICE ARRANGEMENTS

(71) Applicant: Cochlear Limited, Macquarie University, NSW (AU)

(72) Inventor: Koen Van den Heuvel, Hove (BE)

(73) Assignee: Cochlear Limited, Macquarie University (AU)

( * ) Notice: Subject to any disclaimer, the term of this patent is extended or adjusted under 35 U.S.C. 154(b) by 75 days.

(21) Appl. No.: 15/226,084

(22) Filed: Aug. 2, 2016

(65) Prior Publication Data

US 2018/0036537 A1    Feb. 8, 2018

(51) Int. Cl.
| | |
|---|---|
| A61N 1/36 | (2006.01) |
| A61N 1/372 | (2006.01) |
| A61N 1/378 | (2006.01) |
| A61N 1/05 | (2006.01) |
| A61N 1/375 | (2006.01) |

(52) U.S. Cl.
CPC ..... *A61N 1/36032* (2013.01); *A61N 1/36038* (2017.08); *A61N 1/0541* (2013.01); *A61N 1/3787* (2013.01); *A61N 1/37223* (2013.01); *A61N 1/37514* (2017.08); *A61N 1/37518* (2017.08)

(58) Field of Classification Search
None
See application file for complete search history.

(56) References Cited

U.S. PATENT DOCUMENTS

| | | | |
|---|---|---|---|
| 7,003,353 B1 | 2/2006 | Parkhouse | |
| 7,212,864 B2 | 5/2007 | Wahlstrand et al. | |
| 7,317,947 B2 | 1/2008 | Wahlstrand et al. | |
| 8,352,046 B1 | 1/2013 | Haller et al. | |
| 8,397,732 B2 | 3/2013 | Singhal et al. | |
| 2002/0019669 A1* | 2/2002 | Berrang | A61N 1/36036 623/10 |
| 2004/0172102 A1* | 9/2004 | Leysieffer | A61N 1/36036 607/57 |
| 2010/0272299 A1* | 10/2010 | Van Schuylenbergh | H04R 25/554 381/315 |
| 2014/0288620 A1* | 9/2014 | DiLorenzo | A61N 1/36053 607/62 |
| 2016/0094922 A1* | 3/2016 | Ollgaard | H04R 25/606 600/25 |

FOREIGN PATENT DOCUMENTS

EP    2022532 A1    2/2009

* cited by examiner

*Primary Examiner* — Ankit D Tejani
(74) *Attorney, Agent, or Firm* — Edell, Shapiro & Finnan, LLC

(57) ABSTRACT

Embodiments presented herein are generally directed to arrangements for implantable medical devices. The implantable medical devices may include one or more of a single-body calvaria implant and an implantable microphone subcutaneously implanted in the recipient's forehead region.

20 Claims, 15 Drawing Sheets

781(E)

781(F)

781(G)

IMPLANTABLE MEDICAL DEVICE ARRANGEMENTS

BACKGROUND

Field of the Invention

The present invention relates generally to implantable medical devices.

Related Art

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, mechanical stimulators, electro-acoustic devices, cochlear implants, etc.), implantable pacemakers, defibrillators, functional electrical stimulation devices, and other implantable medical devices, have been successful in performing life saving and/or lifestyle enhancement functions for a number of years.

The types of implantable medical devices and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional components perform diagnosis, prevention, monitoring, treatment or management of a disease or injury or symptom thereof, or to investigate, replace or modify of the anatomy or of a physiological process.

SUMMARY

In one aspect a bilateral hearing prosthesis is provided. The bilateral hearing prosthesis comprises: first and second stimulation arrangements associated with a left and right ear, respectively, of a recipient; one or more sound input elements configured to receive sound signals; and a single-body body calvaria implant electrically connected to the first and second stimulation arrangements, and comprising: a hermetically-sealed housing, a bilateral sound processor disposed in the housing, and a bilateral stimulator unit disposed in the housing, wherein the bilateral sound processor and bilateral stimulator unit are configured to convert the sound signals received via the one or more sound input elements into bilateral stimulation signals that are delivered to the recipient via the first and second stimulation arrangements.

In another aspect a method is provided. The method comprises: positioning an implantable module in a recipient, wherein the implantable module includes a sound processor and a stimulator unit; positioning at least one implantable microphone in a recipient's forehead region adjacent to a frontal bone of a recipient's skull; receiving, with the implantable microphone, sound signals through forehead tissue of the recipient; converting the sound signals into electrical stimulation signals; and providing the electrical stimulation signals to the sound processor in the implantable module for conversion into stimulation signals for delivery to the recipient.

In another aspect an implantable medical device system is provided. The implantable medical device system comprises: a single-body body calvaria implant including a rechargeable battery, an implantable radio-frequency (RF) coil, and an implantable magnetic component co-located with the RF coil; and a recharging unit including an external RF coil and a magnet co-located with the external RF coil configured to align the external RF coil with the implantable RF coil to form a transcutaneous inductive charging link for transfer of power signals from the recharging unit to the single-body body calvaria implant.

BRIEF DESCRIPTION OF THE DRAWINGS

Embodiments of the present invention are described herein in conjunction with the accompanying drawings, in which.

DETAILED DESCRIPTION

Embodiments presented herein are generally directed to implantable medical devices that include one or more of a single-body calvaria implant and an implantable microphone subcutaneously implanted in the recipient's forehead region. For ease of illustration, embodiments of the present invention are primarily described herein in connection with certain types of implantable medical device systems, namely totally or mostly implantable auditory or hearing prostheses, such as cochlear implants, auditory brain stimulators, electro-acoustic prostheses, bimodal prostheses, etc. However, it is to be appreciated that embodiments of the present invention may be implemented in any partially or fully implantable medical device now known or later developed.

As used herein, a totally implantable hearing prosthesis is a system in which all components of the hearing prosthesis are configured to be implanted under skin/tissue of the recipient. Because all components of such a hearing prosthesis are implantable, the hearing prosthesis is configured to operate, for at least a period of time, without the need of any external component. As such, a totally implantable hearing prosthesis includes sound input elements, sound processing elements, stimulation delivery elements, and one or more rechargeable power sources that are all implanted within the recipient. A mostly implantable hearing prosthesis is similar to a totally implantable except one or more external elements are needed to perform hearing rehabilitation (e.g., one or more external sound input elements, one or more external power sources, etc.).

Figure 1A:
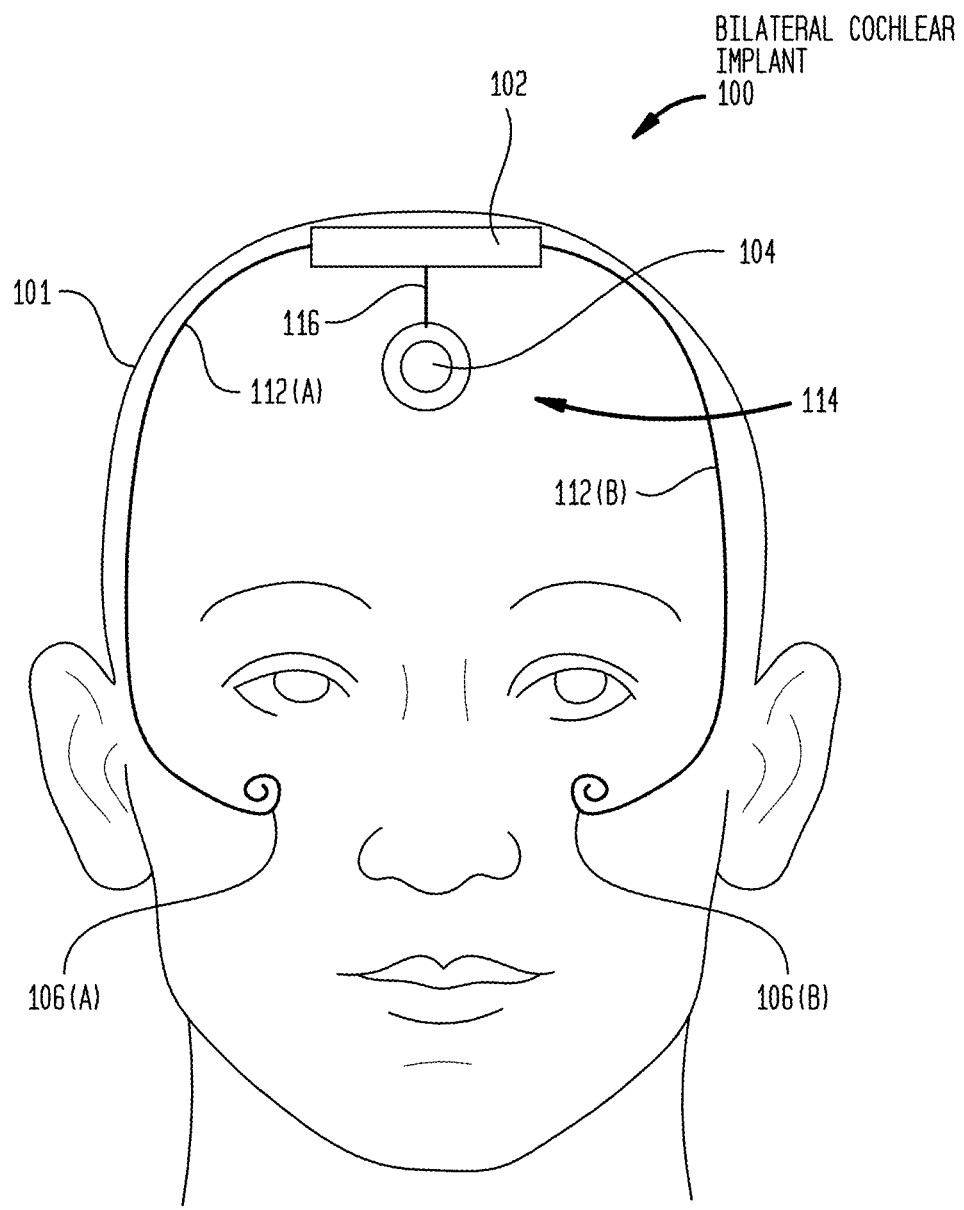
FIG. 1A is a schematic diagram of a bilateral cochlear implant in accordance with embodiments presented herein.
Figure 1B:
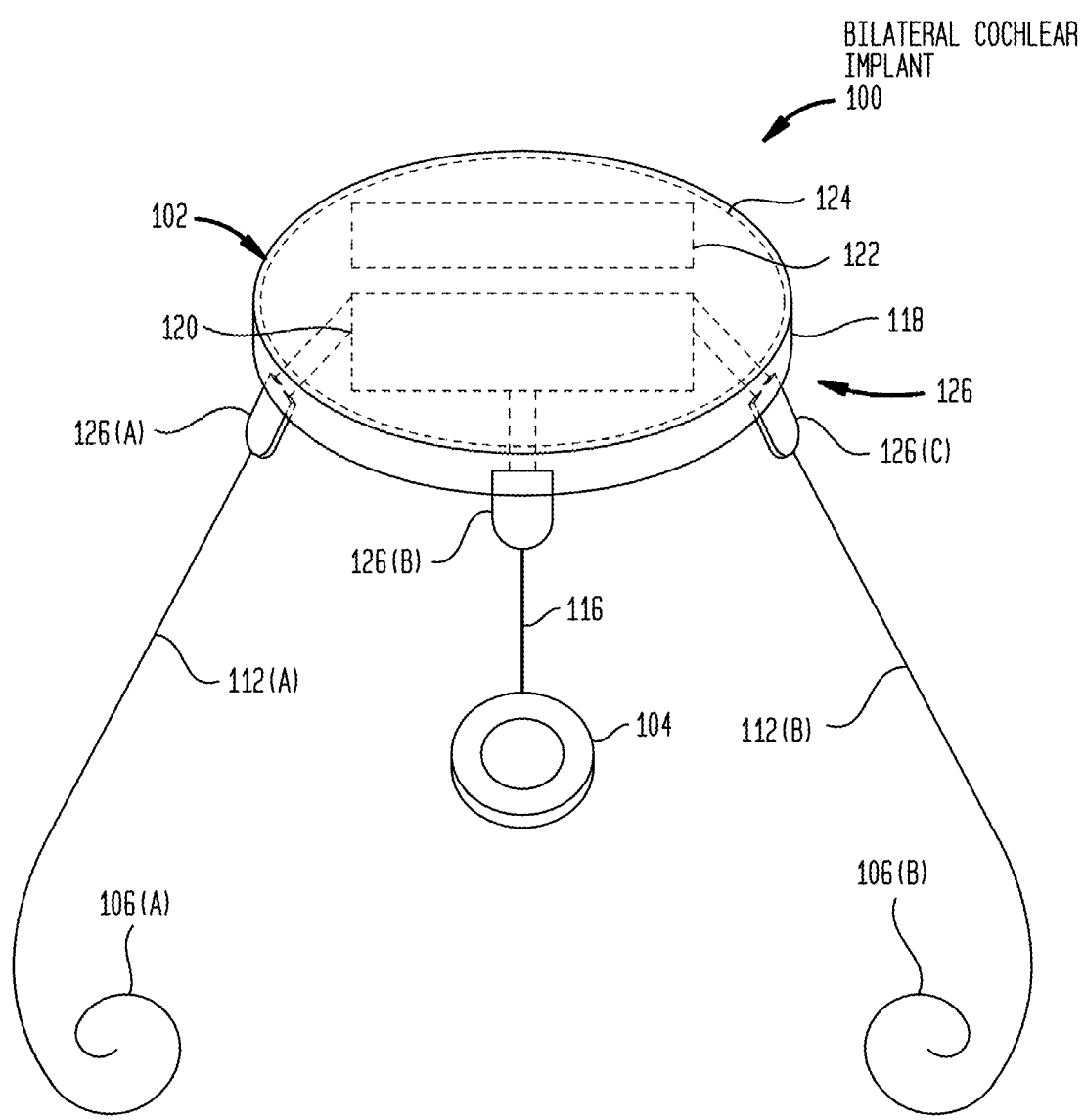
FIG. 1B is a simplified perspective view of the bilateral cochlear implant of FIG. 1A.
Figure 1C:
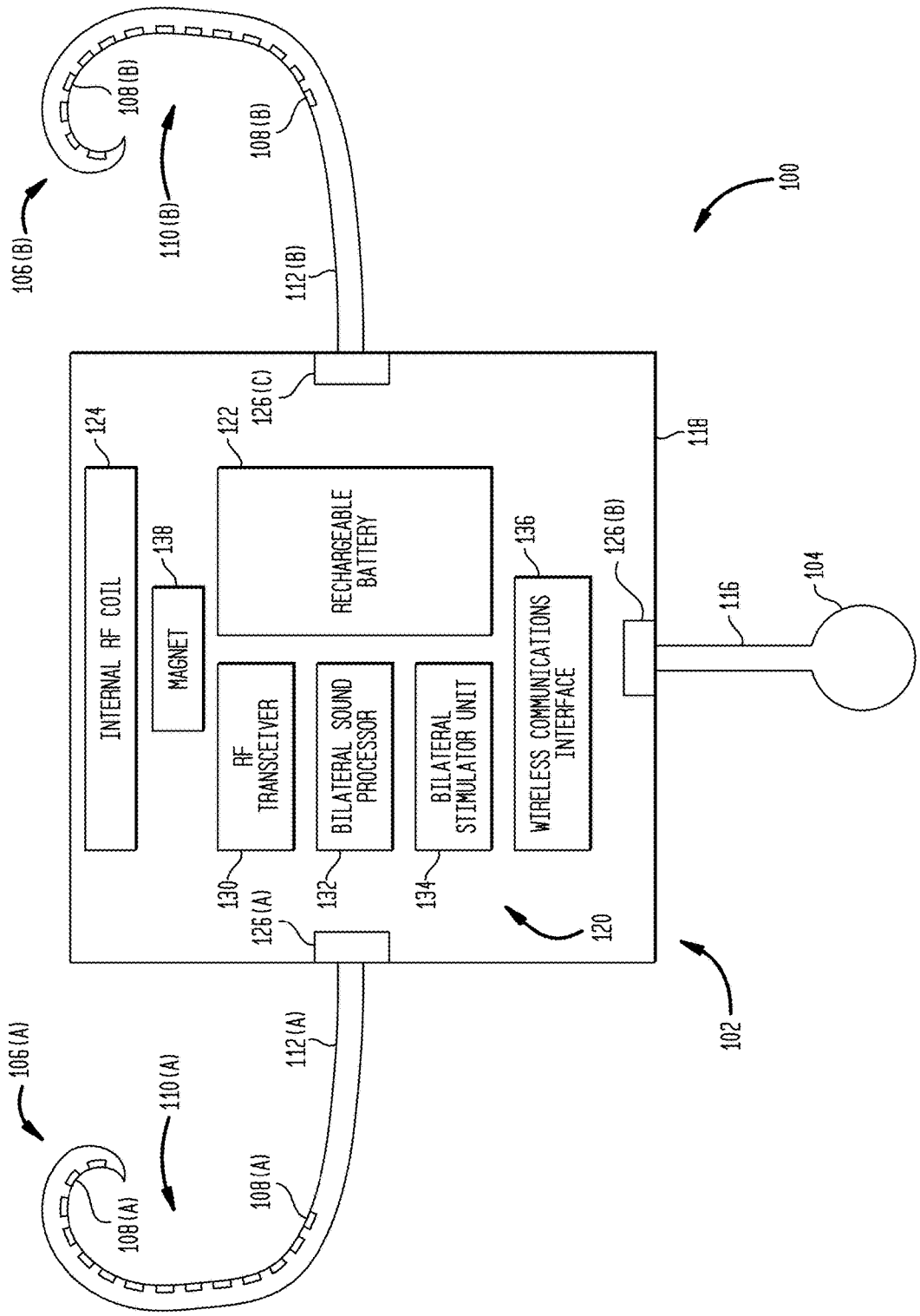
FIG. 1C is a schematic block diagram of the bilateral cochlear implant of FIG. 1A.

FIGS. 1A-1C are diagrams illustrating a totally implantable bilateral hearing prosthesis, namely a totally implantable bilateral cochlear implant 100, in accordance with embodiments presented herein. FIG. 1A is a schematic diagram illustrating the bilateral cochlear implant 100 implanted in the head 101 of a recipient, while FIG. 1B is a simplified perspective view of the bilateral cochlear implant 100 shown separate from the head 101 of the recipient. FIG. 1C is a schematic block diagram illustrating further details of the bilateral cochlear implant 100. For ease of explanation, FIGS. 1A, 1B, and 1C will generally be described together.

The totally implantable bilateral cochlear implant 100 is a single-body device, meaning that a single (i.e., one) implant body/module 102 (i.e., a single housing) is used to control and power two (2) bilaterally-implanted stimulation arrangements (i.e., two stimulation arrangements that are each implanted and configured to stimulate one ear of the recipient). In the embodiments of FIGS. 1A-1C, the bilaterally-implanted stimulation arrangements comprise two intra-cochlea stimulating assemblies 106(A) and 106(B) implanted in opposing inner ears of the recipient.

Also shown in FIGS. 1A-1C is an implantable microphone 104 that is configured to be subcutaneously implanted in the recipient's forehead region 114, namely between the recipient's frontal bone and the tissue (e.g., skin/tissue/fat) covering the frontal bone. That is, as described further below, the implantable microphone 104 has an arrangement so as to be implanted adjacent the recipient's frontal bone such that, after implantation, the implantable microphone can detect sound signals through the recipient's forehead tissue. Such implantable microphones are sometimes referred to herein as implantable forehead microphones. In the example of FIGS. 1A-1C, the implantable forehead microphone 104 is connected to the implant body 102 via an electrical lead 116.

The elongate stimulating assemblies 106(A) and 106(B) are each configured to be at least partially implanted in an inner ear (not shown in FIG. 1A) of the recipient. In particular, stimulating assembly 106(A) is configured to be implanted in the recipient's right-side cochlea, while the stimulating assembly 106(B) is configured to be implanted in the recipient's left-side cochlea. As shown in FIG. 1C, each of the stimulating assemblies 106(A) and 106(B) includes a plurality of intra-cochlear stimulating contacts 108(A) and 108(B), respectively, forming corresponding contact arrays 110(A) and 110(B). The stimulating contacts 108(A) and 108(B) may comprise electrical contacts and/or optical contacts. Each of the stimulating assemblies 106(A) and 106(B) extends through an opening in the corresponding cochlea (e.g., cochleostomy, the round window, etc.) and each has a proximal end connected to the implant body 102 via a lead region 112(A) and 112(B), respectively.

In the embodiments of FIGS. 1A-1C, the implant body 102 is a single-body calvaria implant that is configured to be positioned adjacent to (i.e., on or partially within) the recipient's calvaria (skull cap), which is formed by the superior portions of the recipient's frontal bone and the recipient's parietal bones. In one embodiment, the single-body calvaria implant 102 is configured to be implanted near the sagittal suture connecting the two parietal bones, and/or near a location where the coronal suture connecting frontal bone to parietal bones intersects with the sagittal suture.

As shown in FIG. 1C, the single-body calvaria implant 102 includes a hermetically-sealed housing 118 in which electronics 120, a rechargeable power source (e.g., rechargeable battery) 122, and an implantable radio-frequency (RF) coil 124 are positioned. The implant body 102 also comprises a plurality of hermetic electrical connectors 126 that enable the electronics 120 within the housing to be connected to functional components located outside of the housing 118. In the specific arrangement of FIG. 1C, three hermetic electrical connectors 126(A), 126(B), and 126(C) are shown for connecting the lead 112(A), lead 116, and lead 112(B), respectively, to the electronics 120. However, it is to be appreciated that single-body calvaria implants in accordance with embodiments presented herein may include different numbers of electrical connectors.

The use of hermetic electrical connectors 126(A), 126(B), and 126(C) advantageously allows the single-body calvaria implant 102 to be physically and electrically separated from the stimulating assemblies 106(A) and 106(B) and the implantable forehead microphone 104. As such, the single-body calvaria implant 102 may be explanted and replaced without disturbing the implanted location of the stimulating assemblies 106(A) and 106(B) and/or the implantable forehead microphone 104. It may be desirable to explant and replace the single-body calvaria implant 102 without disturbing the stimulating assemblies 106(A) and 106(B) when, for example, the rechargeable battery 122 has reached the end of its useable life, new technology becomes available, etc.

Although FIGS. 1A-1C have been described with reference to a cochlear implant, it is also to be appreciated that the use of hermetic electrical connectors 126(A), 126(B), and 126(C) may, in certain arrangements, enable the single-body calvaria implant 102 to operate as a modular device that supports different types of stimulation arrangements.

FIG. 1C illustrates further details of the single-body calvaria implant 102. In particular, FIG. 1C illustrates that the electronics 120 within housing 118 comprise an RF transceiver 130, a bilateral sound processor 132, a bilateral stimulator unit 134, and, in certain arrangements, a wireless communications interface 136. For ease of illustration, electrical connections between the various elements of the single-body calvaria implant 102 have been omitted from FIG. 1C.

Also shown in FIG. 1C is a magnetic element, such as a magnet 138, that is co-located with, and fixed relative to, the implantable RF coil 124. In general, the magnet 138 is located in the geometric center of the implantable RF coil 124.

In operation, the implantable forehead microphone 104 is configured to detect/receive sound signals through the recipient's forehead tissue and to generate electrical signals representative of the received sound signals. These electrical signals are then provided to the bilateral sound processor 132. The bilateral sound processor 132 implements one or more speech processing and/or coding strategies to convert the electrical signals output by the microphone into data signals for use by bilateral stimulator unit 134. Bilateral stimulator unit 134 utilizes the data signals received from the bilateral sound processor 132 to generate electrical stimulation (current) signals for delivery to the left-side cochlea and the right-side cochlea of the recipient via stimulating assembly 106(A) and 106(B), respectively. That is, the bilateral sound processor 132 and the bilateral stimulator unit 134 collectively operate to convert sound signals received via the implantable microphone 104 into bilateral stimulation signals that are delivered to the recipient via stimulating assembly 106(A) and 106(B). As used herein, bilateral stimulation signals are current signals that are generated by one (i.e., a single) arrangement of a sound processor and stimulator unit (i.e., the bilateral sound processor and bilateral stimulator unit) within a single-body implant, where the sound processor and stimulator unit arrangement is able to process sound signals detected by the same set of one or more sound input elements and is capable of providing stimulation signals to one or both of bilaterally implanted stimulation arrangements. In general, the bilateral sound processor 132 makes use of a "map" or "program" that is the same, or accounts for, both ears of the recipient. The bilateral sound processor 132 may also ensure the same volume setting in both ears, selectively active certain dynamic sound processing features (e.g., automatic gain control), etc.

The wireless interface 136 is a short-range wireless transceiver configured for wireless communication with an external device in accordance with a short-range wireless standard (i.e., over a short-range wireless link/connection). For example, the wireless interface 136 may be a Bluetooth® transceiver that communicates using short-wavelength Ultra High Frequency (UHF) radio waves in the industrial, scientific and medical (ISM) band from 2.4 to 2.485 gigahertz (GHz). Bluetooth® is a registered trademark owned by the Bluetooth® SIG. It is to be appreciated that other types of wireless interfaces may be used in accordance with embodiments presented herein.

As noted, the single-body calvaria implant 102 also comprises the implantable RF coil 124, the RF transceiver 120, and the magnet 138. The implantable RF coil 124 is a wire antenna coil comprised of multiple turns of electrically insulated single-strand or multi-strand platinum or gold wire. As described further below, the RF transceiver 120 is configured to transcutaneously receive power and/or data from an external charging device via the implantable RF coil 124.

Figure 2:
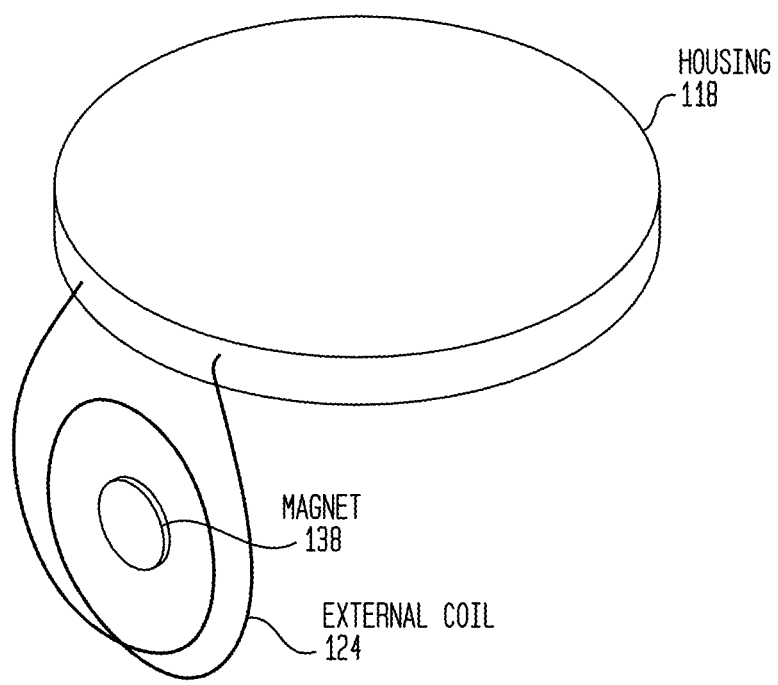
FIG. 2 is a perspective view of a single-body calvaria implant in accordance with embodiments presented herein.

Although FIGS. 1B and 1C illustrate the implantable RF coil 124 within the housing 118, it is to be appreciated that in alternative embodiments the RF coil 124 may be located external to the housing 118. For example, FIG. 2 illustrates an arrangement in which the implantable RF coil 124 is outside the housing 118. In these embodiments, the electrical insulation of the implantable RF coil 124 is provided by a flexible molding (e.g., silicone molding), which has been omitted from FIG. 2 for ease of illustration. The implantable RF coil 124 is connected to the transceiver 130 via a hermetic feedthrough or a hermetic electrical connector. As shown, the magnet 138 is generally located in the center of the implantable RF coil 124, which, in this illustrative example, is offset from the housing 118.

Returning to the embodiments of FIGS. 1A-1C, as noted above the single-body calvaria implant 102 controls and powers both of the implanted stimulating assemblies 106(A) and 106(B). That is, the bilateral sound processor 132 and the bilateral stimulator unit 134 are operable to convert sound signals received via the implantable microphone 104 into bilateral stimulation signals that are delivered to the recipient via two separate stimulation arrangements. Because the same sound processor and stimulator unit are used to generate the bilateral stimulation signals, the bilateral stimulation signals are synchronized/coordinated at both ears of the recipient. In this way, the embodiment of FIGS. 1A-1C illustrate an integrated bilateral system that is significantly different from conventional arrangements that use independent cochlear implants, having separate power sources, separate sound processing, separate microphones, separate stimulator units, etc., at each of the left and right ears of a recipient.

The integrated bilateral system of FIGS. 1A-1C may be advantageous to systems that use independent cochlear implants for a number of reasons. For example, the integrated bilateral system reduces the number of implanted components (e.g., a single rechargeable battery), thereby providing a lower cost implant. In addition, in the integrated bilateral system of FIGS. 1A-1C, fully-coordinated bilateral processing is possible for the first time since the processing and stimulation signal generation for each of the bilateral stimulation arrangements is combined into a single sound processor and stimulator unit arrangement. In addition, and as described further below, the integrated bilateral system of FIGS. 1A-1C provides a sleep-suitable charging arrangement that has the ability to maintain hearing capabilities while the recipient is asleep.

In summary, FIGS. 1A-1C illustrate a bilateral cochlear implant having a single implantable module configured to drive bilaterally implanted stimulating assemblies, one in each of the left and right ear of the recipient. It is to be appreciated that, for ease of illustration, in FIGS. 1A-1C the sizes of the implant body 102, implantable microphone 104, and the stimulating assemblies 106(A) and 106(B), have been exaggerated, relative to the illustrated size of the recipient's head 101.

The embodiments of FIGS. 1A-1C also illustrate the use of a single implantable forehead microphone located at a recipient's forehead region as an input for the bilateral sound processing operations. That is, FIGS. 1A-1C illustrate a totally implantable bilateral cochlear implant 100 that operates in an "invisible mode," meaning that, during normal use for hearing rehabilitation, no elements of the system are visible to others. However, it is to be appreciated that embodiments of the present invention may use additional microphones or other sound input elements, including additional implantable microphones or external sound input elements.

Figure 3:
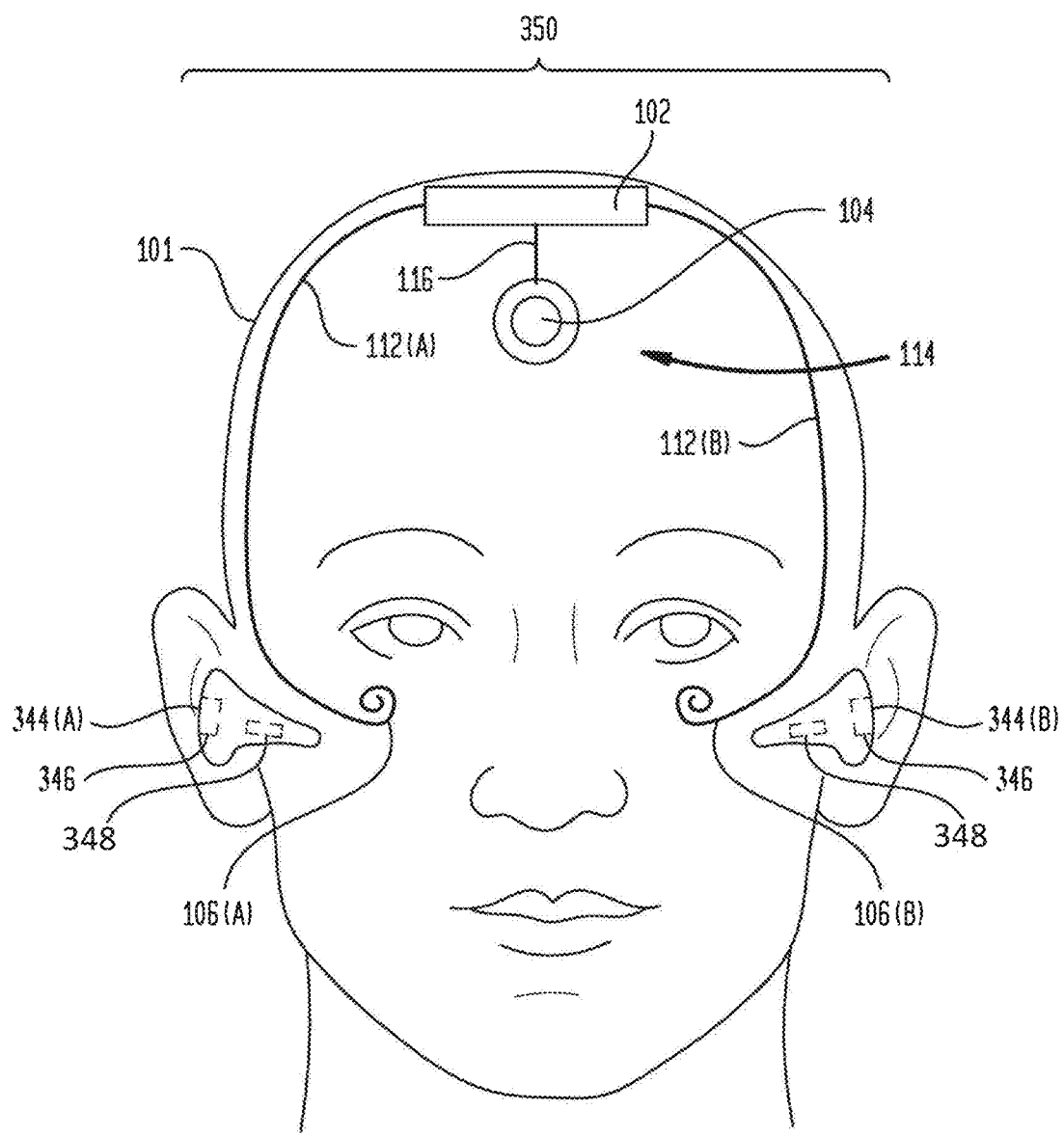
FIG. 3 is a schematic diagram of a bilateral cochlear implant system in accordance with embodiments presented herein.

For example, FIG. 3 illustrates a further embodiment in which the totally implantable bilateral cochlear implant 100 operates in an "external hearing mode" that makes use of one or more external sound input devices 344(A) and 344(B). In the example of FIG. 3, the external sound input devices 344(A) and 344(B) are in-the-ear (ITE) microphone units configured to be positioned in the left and right ears, respectively, of the recipient. As shown, each of the microphone units 344(A) and 344(B) includes a microphone 346 and a wireless transmitter 348.

In operation, the microphones 346 are configured to detect and convert sound signals into electrical signals representative of the received sound signals. The wireless transmitters 348 are configured to send (e.g., wirelessly stream) these electrical signals to the wireless communications interface 136 (FIG. 1C) in the single-body calvaria implant 102. As such, the bilateral sound processor 132 is configured to process the sound signals received at the microphone units 344(A) and 344(B), as well as at the implantable microphone 104 positioned on the frontal bone of the recipient. Such arrangements provides high levels of directionality and preservation of bilateral cues, since the sound processing is based on inputs received from three primary directions (i.e., directly to the left, directly to the right, and directly to the front of the recipient).

In FIG. 3, the totally implantable bilateral cochlear implant 100 and the microphone units 344(A) and 344(B) form a cochlear implant system 350. It is to be appreciated that such cochlear implant systems may include additional or alternative elements, such as different sound input elements, in accordance with embodiments presented herein. For example, one or more of the microphone units could be replaced by a streaming audio device, such as a radio receiver, a telecoil receiver, etc.

It is to be appreciated that the use of ITE sound input devices with bilateral cochlear implant 100 is merely illustrative, and that other types of external sound input devices may be used in other embodiments, including external behind-the-ear (BTE) sound input devices, body-worn sound input devices, etc.

In the embodiments of FIG. 3, the bilateral sound processor 132 is configured to operate based on one, two, three, or more sound inputs received from any combination of the implantable forehead microphone 104, microphone units 344(A) and 344(B), or other external sound input elements. As such, the arrangement of FIG. 3 provides a recipient with the flexibility to balance hearing performance with aesthetics or other factors. For example, the arrangement of FIG. 3 allows the recipient to choose improved hearing performance in certain settings (e.g., concerts, lectures, cocktail parties, etc.) by making use of the microphone units 344(A) and 344(B) in combination with the implantable forehead microphone 104, or to choose reduced herein performance in other settings (e.g., swimming, sleeping, etc.) by making use of only the implantable forehead microphone 104. As noted elsewhere herein, the implantable forehead microphone 104, due to its position on the recipient's frontal bone, provides improved directionality relative to conventional arrangements where a microphone is located on the side of the recipient's head.

In certain embodiments, the bilateral sound processor 132 is bilateral sound processor 132 is configured to determine, for example, the number, type, and/or location of sound input inputs in use and is configured to dynamically adjust its operation based thereon (e.g., dynamically adjust the implemented sound processing algorithms based on the number or type of inputs and/or relative locations).

As noted above, the single-body calvaria implant 102 includes a rechargeable power source 122, such as a rechargeable battery, that is configured to power the various other implantable elements of the bilateral cochlear implant 100 for at least a period of time without the need for power to be supplied from an external power source. This period of time corresponds to the time it takes for the rechargeable battery 122 to become depleted, which is dictated, for example, by the size of the rechargeable battery 122, mode of operation of the cochlear implant 100, sound environment, etc. However, after the rechargeable battery 122 is depleted, there is a need to recharge the battery from an external power source. Embodiments presented herein may advantageously provide sleep-suitable recharging arrangements.

More specifically, an advantage of the use of a single-body calvaria implant for powering and controlling a bilateral system is that the battery (or batteries) in the single-body can be recharged at night, while the recipient is asleep, in a non-obtrusive and safe manner. As such, hearing prosthesis systems in accordance with embodiments presented herein may include a wireless recharging unit that can be safety used by the recipient to recharge the single-body calvaria implant at night or other times, as needed.

Since the single-body calvaria implant 102 is generally located on the top of the recipient's skull, the implantable RF coil 124 is likely to be accessible while a recipient is asleep. That is, when the recipient is sleeping in a large number of common positions (e.g., on his/her back, on his/her side, partially upright, etc.), it is unlikely and uncommon for the top of the head to be covered by, for example, a pillow. Similarly, the location of the implantable forehead microphone 104 at the recipient's forehead region also makes it likely that the implantable forehead microphone is uncovered while the recipient is sleeping in a large number of common positions (e.g., on his/her back, on his/her side, partially upright, etc.). As such, the implantable forehead microphone 104 will continue to receive sound signals at night with good directionality.

Figure 4A:
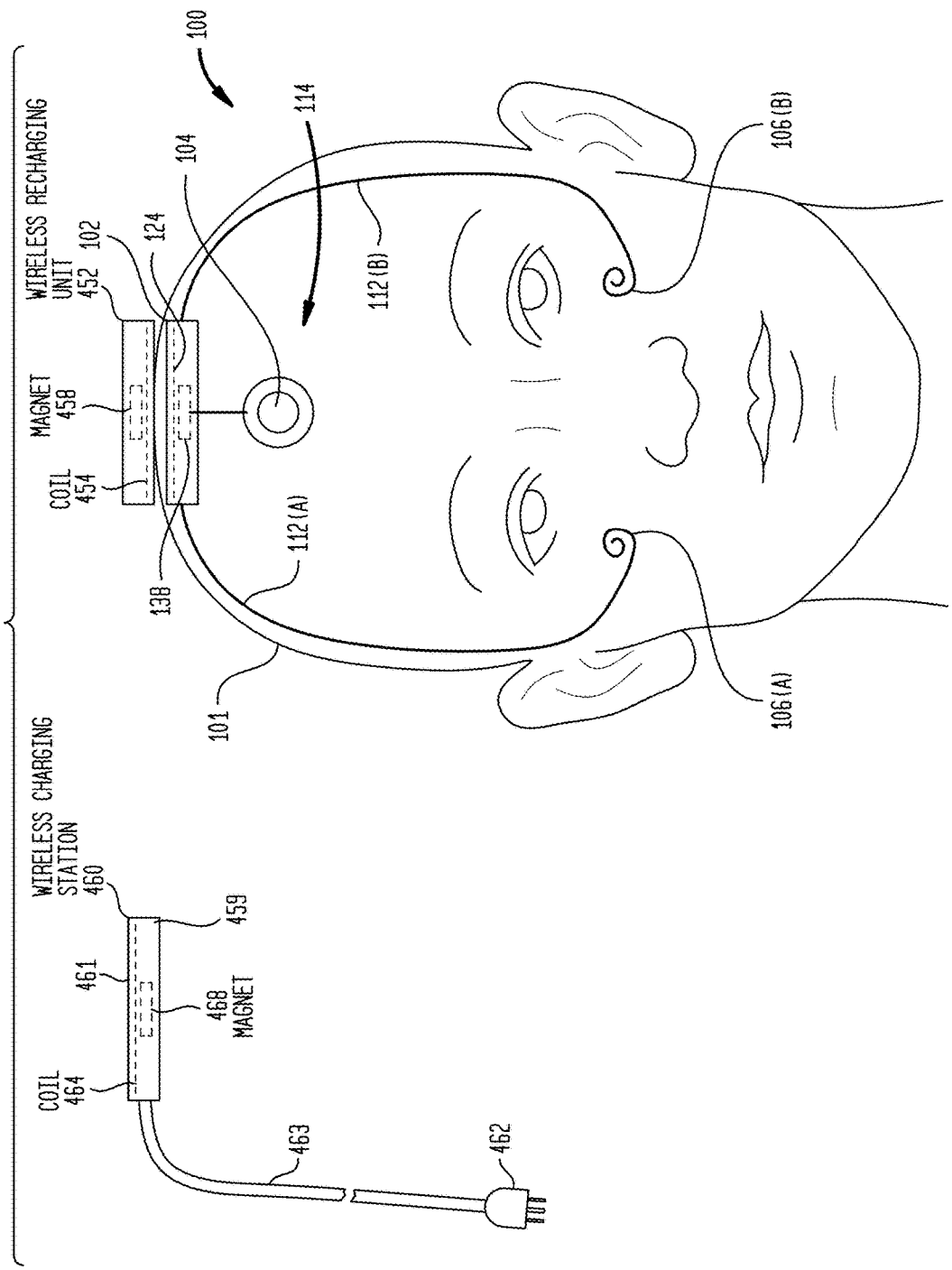
FIG. 4A is a schematic diagram of another bilateral cochlear implant system in accordance with embodiments presented herein.
Figure 4B:
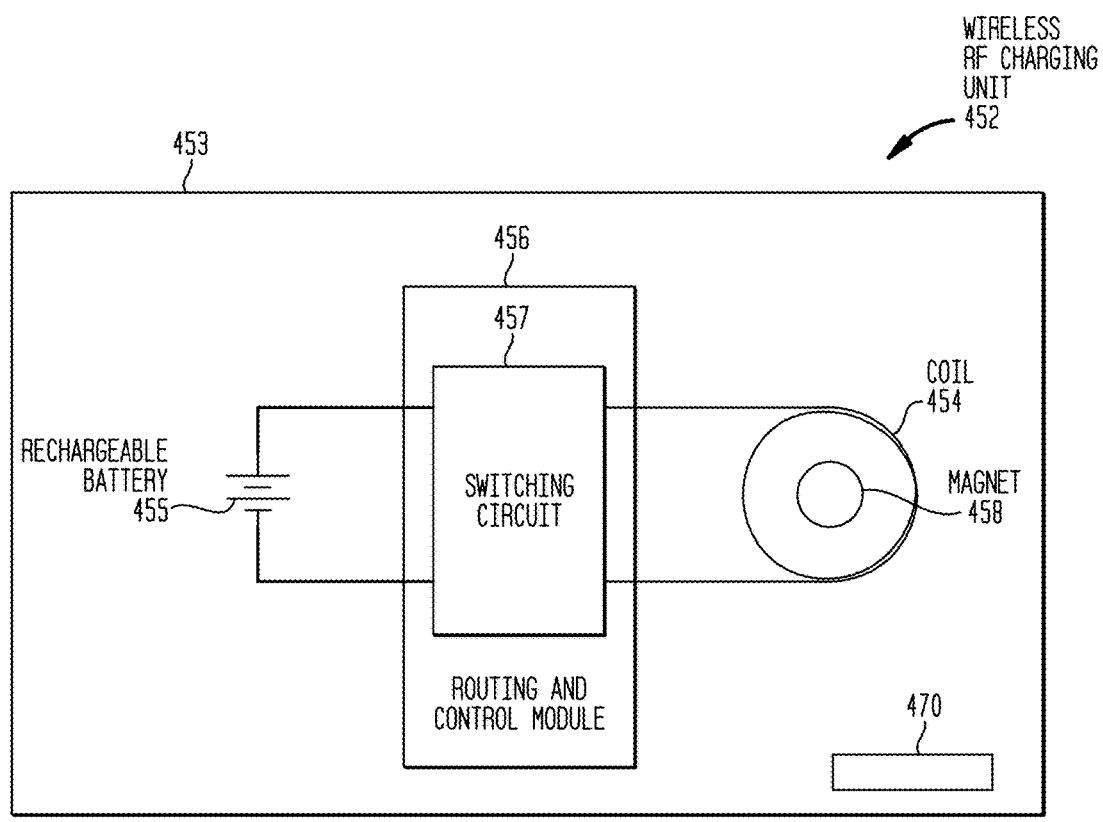
FIG. 4B is a schematic block diagram of a wireless recharging unit in accordance with embodiments presented herein.

FIGS. 4A and 4B are diagrams illustrating a single-body bilateral hearing prosthesis system 450 for recharging an implanted battery while a recipient is, for example asleep (i.e., a sleep-suitable recharging arrangement in accordance with embodiments present herein). More particularly, FIG. 4A is a schematic diagram illustrating a bilateral cochlear implant system 450 that includes the bilateral cochlear implant 100, a wireless recharging unit 452, and a wireless charging station (pad) 460. FIG. 4B is schematic block diagram illustrating further details of the wireless recharging unit 452. For ease of description, FIGS. 4A and 4B will be described together.

The wireless recharging unit 452 comprises a rechargeable battery 455, a routing and control module 456, a magnet 458, and an RF coil 454 disposed in a housing 453. The wireless charging station 460 comprises an RF coil 464, a magnet 468, a cord 463, and a plug 462 for connection to an alternating current (AC) power supply. The wireless charging station 460 also comprises a housing 459 with a surface 461 on which the wireless recharging unit 452 may be positioned.

In operation, the wireless charging station 460 is connected to an AC power supply via the cord 463 and the plug 462, and the wireless recharging unit 452 is "docked" with the wireless charging station 460. That is, the wireless recharging unit 452 is placed on the surface 461 of the wireless charging station 460 and the magnets 468 and 458 are magnetically coupled to one another so as to positon the wireless recharging unit 452 at an appropriate location on the surface 461. The magnetic coupling of the magnets 468 and 458 in the wireless charging station 460 and the wireless recharging unit 452, respectively, facilitate the operational alignment of the RF coil 454 with the RF coil 464.

The operational alignment of the RF coils 454, 456 enables the wireless charging station 460 to transmit power/ energy signals to the wireless recharging unit 452 via a closely-coupled RF link. More specifically, the wireless charging station 460 comprises one or more components (not shown in FIG. 4A) that are configured to use current supplied from the AC power supply to drive the coil 461 so as to induce current flow in the coil 454 of the wireless recharging unit 452 (when the wireless recharging unit 452 is placed on surface 461). The routing and control module 456 is configured to deliver the current induced in the coil 454 to the rechargeable battery 455, thereby recharging the battery 455.

In certain embodiments, the wireless recharging unit 452 comprises a user interface 470. The user interface 470 may be used to indicate the status of the battery 455 (i.e., low battery, fully charged, a percent of charge, etc.), a status of the recharging process, or other information. As such, the user interface 452 may comprise one or more visual indicators, such as light-emitting diodes (LEDs), a liquid crystal display (LCD) display, etc.

Once the rechargeable battery 455 has been recharged above a threshold level, possibly as indicated by the user interface 470, the wireless recharging unit 452 can be removed from the surface 461 of the wireless charging station 460 and, as shown in FIG. 4A, the wireless recharging unit 452 can be "docked" with the single-body calvaria implant 102. That is, as noted above, and as shown in FIG. 4A, the wireless recharging unit 452 is placed on the top of the recipient's head 101 and the magnets 458 and 138 in the wireless recharging unit 452 and he single-body calvaria implant 102, respectively, are magnetically coupled to one another so as to positon the wireless recharging unit 452 at an appropriate location on the recipient' head 101.

The magnetic coupling of the magnets 138 and 458 in the single-body calvaria implant 102 and the wireless recharging unit 452, respectively, facilitate the operational alignment of the RF coil 454 with the implantable RF coil 124. The operational alignment of the coils 454 and 124 enables the wireless recharging unit 452 to transmit power signals to the single-body calvaria implant 102 via a closely-coupled RF link. More specifically, the routing and control module 456 in the wireless recharging unit 452 is configured to use current supplied from the rechargeable battery 455 to drive the coil 454 and thereby induce current flow in the implantable RF coil 124 of the single-body calvaria implant 102. The RF transceiver 130 in the single-body calvaria implant 102 is configured to deliver the current induced in the coil 124 to the rechargeable battery 122, thereby recharging the battery 122.

As noted above, the magnets 138 and 458 in the single-body calvaria implant 102 and the wireless recharging unit 452, respectively, operate to align the coils 454 and 124 so as to enable the transcutaneous transfer of power from the wireless recharging unit 452 to the single-body calvaria implant 102. In addition, the magnets 138 and 458 have sufficient magnetic coupling strength so as to retain the wireless recharging unit 452 on the head of the recipient during normal operation (i.e., to couple the wireless recharging unit 452 to the head 101 of the recipient).

Also noted above, the wireless recharging unit 452 is configured to both receive power signals (current) via coil 454 for charging battery 455 and to send power signals to the single-body calvaria implant 102 via the coil 454. The dual-use of the coil 454 for both receiving and sending power signals is enabled by the routing and control module 456. The routing and control module 456 includes, among other elements, a switching circuit 457 that has a first arrangement that routes received current to the correct terminal of the battery 455, and a second arrangement that routes current from the battery to the correct terminal of the coil 454 during transmission of power.

In accordance with embodiments presented herein, the arrangement of the switching circuit 457 is automatically changed based on whether the wireless recharging unit 452 is in proximity to the wireless charging station 460 or the single-body calvaria implant 102. In one form, the wireless recharging unit 452 is configured to use variations in detected electrical characteristics to change the arrangement of the switching circuit 457. In another form, the wireless recharging unit 452 and the wireless charging station 460 each include a short-range wireless transceiver so that the wireless recharging unit 452 can use wirelessly communicated information to change the arrangement of the switching circuit 457.

As noted, FIGS. 4A-4B illustrate an example of a sleep-suitable recharging arrangement, meaning that the recharging is safe for substantially all recipients while they are asleep (e.g., no cord that could pose a strangulation risk), and the charging can occur when the recipient is in a prone position. That is, the positioning of the wireless recharging unit 452 adjacent the recipient's calvaria allows the recipient to sleep on the back of the head or either side of the head without interfering with the recharging operation.

Although FIGS. 4A and 4B have been primarily described with reference to the use of the wireless recharging unit 452 while a recipient is sleeping, it is to be appreciated that the location of the wireless recharging unit 452 also allows for recharging during other activities. It is also to be appreciated that wireless recharging unit 452 could be built into one or more products that are designed to be worn on the head of a recipient, such as hats, toupees/wigs, etc.

Figure 5:
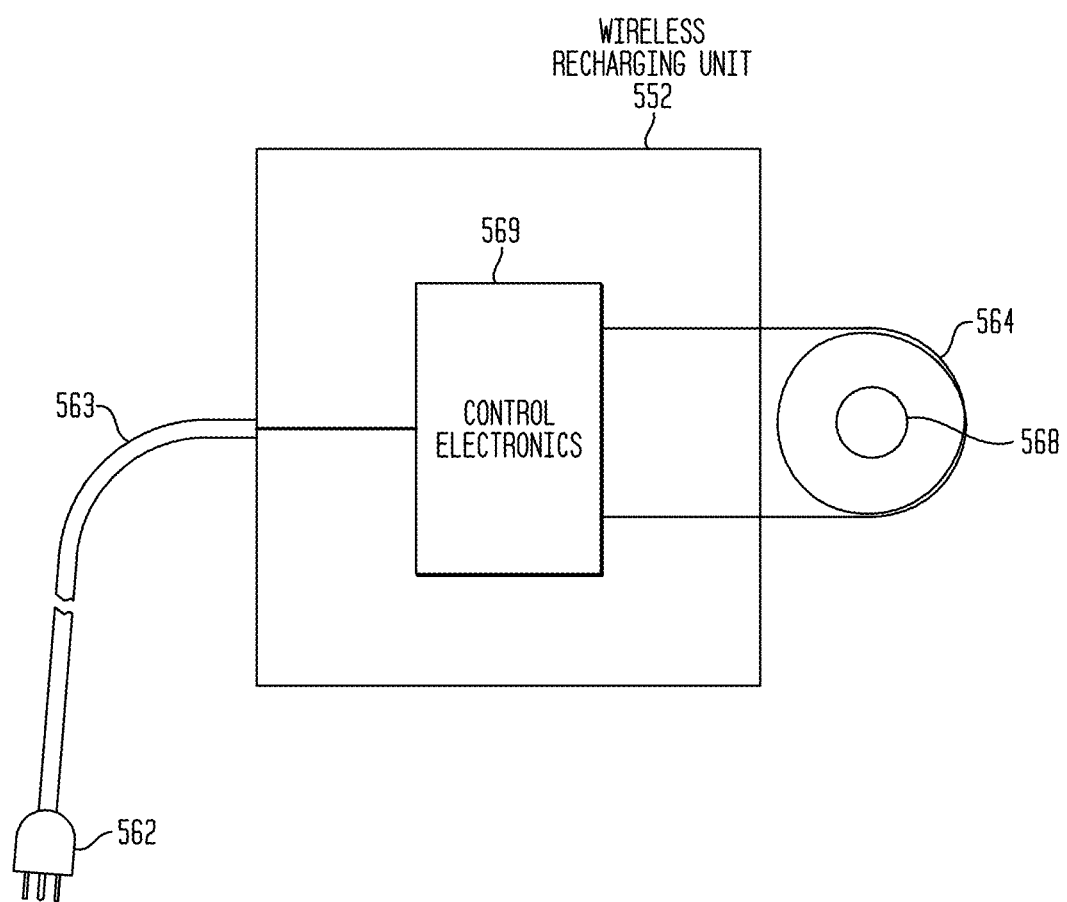
FIG. 5 is a schematic block diagram of a wired recharging unit in accordance with embodiments presented herein.

It is to be appreciated that the wireless recharging arrangement of FIGS. 4A-4B is illustrative and that other charging arrangements may be used in further embodiments presented herein. For example, FIG. 5 is a schematic block diagram illustrating an embodiment of a wired recharging unit 552 that may be used to recharge a single-body calvaria implant, such the single-body calvaria implant 102. In the embodiment of FIG. 5, the wired recharging unit 552 is configured to be directly connected to an AC power supply and, as such, comprises an RF coil 564, a magnet 568, control electronics 569, a power cord 563, and a plug 562.

In operation, the wired recharging unit 552 is connected to the AC power supply via power cord 563 and plug 562, and the unit is placed on the top of the recipient's head 101. The magnets 568 and 138 in the recharging unit 552 and the single-body calvaria implant 102, respectively, facilitate the operational alignment of the coil 564 with the implantable RF coil 124. The operational alignment of the coils 564, 124 enables the recharging unit 552 to transmit power to the single-body calvaria implant 102 via a closely-coupled RF link. More specifically, the control electronics 569 are configured to use current supplied from the AC power supply to drive the coil 564 and thereby induce current flow in the coil 124 of the single-body calvaria implant 102 (when the recharging unit 552 is placed on the top of the recipient's head). The magnets 138 and 568 also have sufficient magnetic coupling strength so as to retain the recharging unit 552 on the top of the head 101 of the recipient during the recharging process.

As noted above, totally implantable hearing prostheses in accordance with embodiments presented herein make use of a single-body calvaria implant to control stimulation arrangements (e.g., stimulation assemblies) at both ears of a recipient. Single-body calvaria implants in accordance with embodiments presented herein may have a number of different shapes designed to be implanted adjacent a recipient's calvaria where, in certain examples, the implant is not readily visible to others and is connectable to the two stimulation arrangements.

Figure 6A:
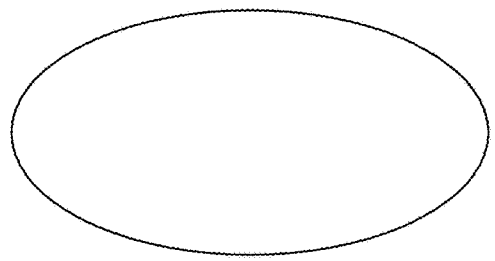
FIGS. 6A-6E are diagrams illustrating example shapes for single-body calvaria implants in accordance with embodiments presented herein.

FIGS. 6A-6E and 7A-7G are diagrams illustrating example shapes for single-body calvaria implants in accordance with embodiments presented herein. More specifically, FIG. 6A is a top view of an example single-body calvaria implant, while FIGS. 6B-6E are simplified cross-sectional views that correspond to the top view of FIG. 6A. That is, FIGS. 6B-6E each illustrate a different possible cross-section for an implant having the top shape of FIG. 6A.

Figure 7A:
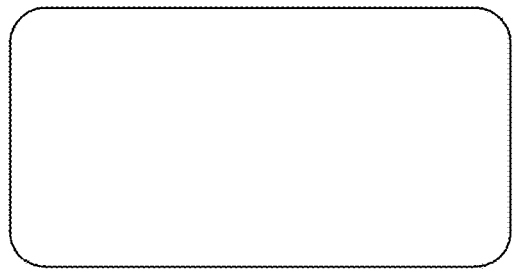
FIGS. 7A-7G are diagrams illustrating further example shapes for single-body calvaria implants in accordance with embodiments presented herein.

Similarly, FIG. 7A is a top view of another example single-body calvaria implant, while FIGS. 7B-7G are simplified cross-sectional views that correspond to the top view of FIG. 7A. That is, FIGS. 7B-7G each illustrate a different possible cross-section for an implant having the top shape of FIG. 7A.

Figure 6B:
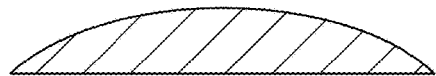
Figure 6D:
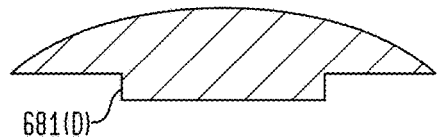
Figure 6C:
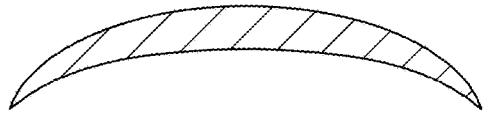
Figure 6E:
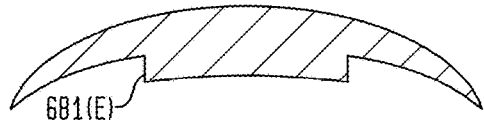
Figure 7B:
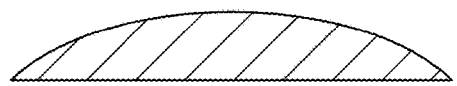
Figure 7E:
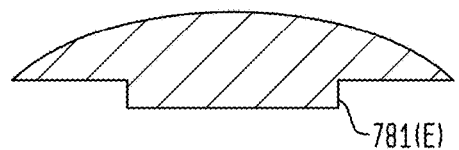
Figure 7C:
Figure 7F:
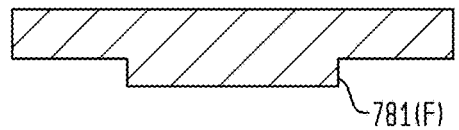
Figure 7D:
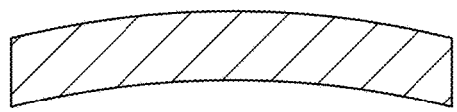
Figure 7G:
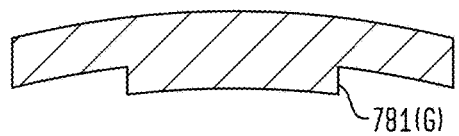

FIGS. 6B and 6C, as well as FIGS. 7B, 7C, and 7D, all illustrate cross-sectional shapes for single-body calvaria implants that are implantable so as to rest along a flat or curved portion of the recipient's skull bone. In contrast, FIGS. 6D and 6E, as well as FIGS. 7E, 7F, and 7G illustrate cross-sectional shapes each having an extension or pedestal 681(D), 681(E). 781(E), 781(F), and 781(G), respectively, that is designed to fit into a surgically-created opening formed in the recipient's skull bone.

Figure 8A:
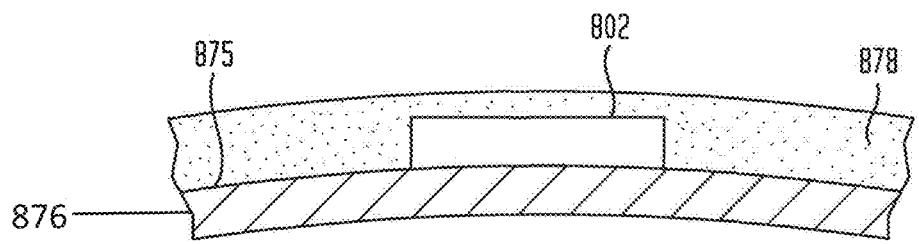
FIGS. 8A-8C illustrate three possible implanted configurations for a single-body calvaria implant in accordance with embodiments presented herein.
Figure 8B:
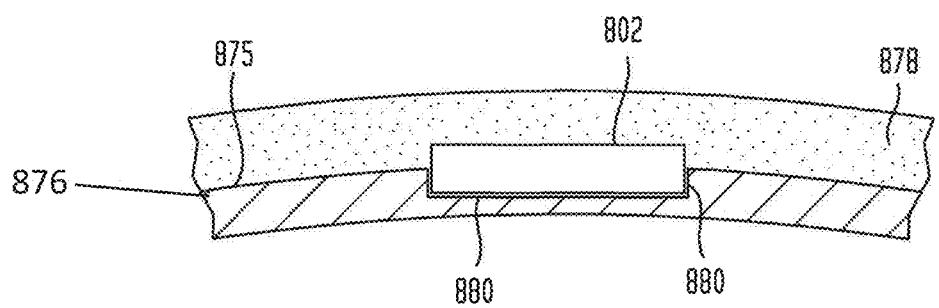
Figure 8C:
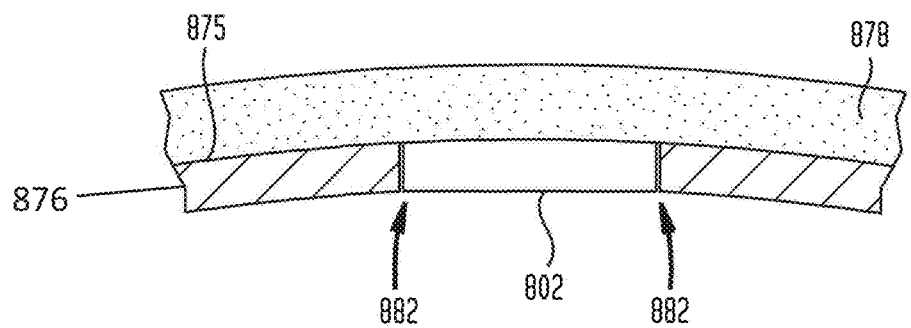

FIGS. 8A-8C illustrate three possible implanted configurations for a single-body calvaria implant in accordance with embodiments presented herein. In particular, FIG. 8A illustrates a single-body calvaria implant 802 that is implanted on an outer surface 875 of a recipient's skull bone 876. As shown, the single-body calvaria implant 802 is located between the outer surface 875 of the skull bone 876 and the recipient's skin/tissue 878.

FIG. 8B illustrates the single-body calvaria implant 802 implanted within a surgically-created pocket 880 formed in the recipient's skull bone 876. In FIG. 8B, the pocket 880 extends only partially through the recipient's skull bone 876. FIG. 8C illustrates the single-body calvaria implant 802 implanted within a surgically-created aperture 882 formed in the recipient's skull bone 876. Unlike the pocket 880 of FIG. 8B, the aperture 882 extends entirely through the recipient's skull bone 876.

Figure 9A:
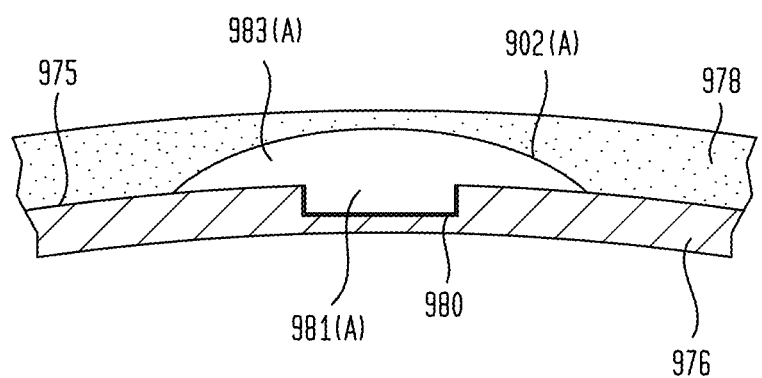
FIGS. 9A and 9B illustrate implanted configurations for two single-body calvaria implants in accordance with embodiments presented herein.
Figure 9B:
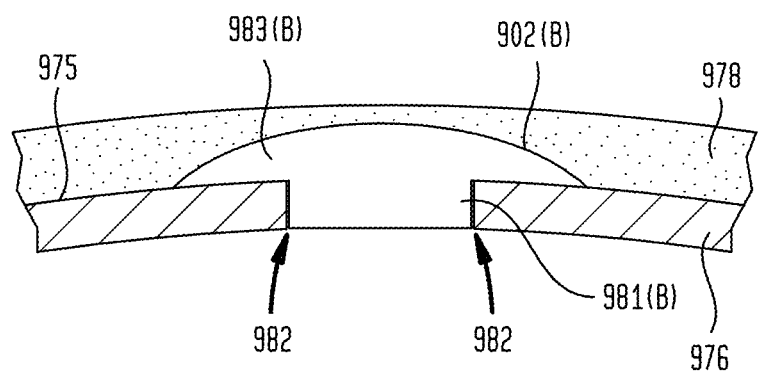

As noted, FIGS. 6D, 6E, 7E, 7F, and 7G illustrate cross-sectional shapes of single-body calvaria implants that each have a pedestal that is designed to fit into a surgically-created opening formed in the recipient's skull bone. FIGS. 9A and 9B illustrate implanted arrangements for two single-body calvaria implants 902(A) and 902(B), respectively, having such pedestals.

More specifically, FIG. 9A illustrates the single-body calvaria implant 902(A) having a pedestal 981(A) that is implanted within a surgically-created pocket 980 formed in the recipient's skull bone 976. In FIG. 9A, the pocket 980 extends only partially through the recipient's skull bone 976 from the outer surface 975. As such, a main portion 983(A) of the of the single-body calvaria implant 902(A) is located on the outer surface 975 of the skull bone 976, while the pedestal 981(A) extends into the skull bone 976. The main portion 983(A) is located between the outer surface 975 and the recipient's skin/tissue 978.

FIG. 9B illustrates the single-body calvaria implant 902(B) having a pedestal 981(B) that is implanted within a surgically-created aperture 982 formed in the recipient's skull bone 976. Unlike the pocket 980 of FIG. 9A, the aperture 982 extends entirely through the recipient's skull bone 976. As such, in FIG. 9B, a main portion 983(B) of the of the single-body calvaria implant 902(B) is located on the outer surface 975 of the skull bone 976, while the pedestal 981(B) extends substantially through the skull bone 976.

As noted, certain embodiments presented herein are directed to an implantable forehead microphone that is configured to be implanted at a recipient's forehead region, namely between the recipient's frontal bone and the forehead tissue (e.g., skin/tissue/fat) covering the frontal bone. Implantable forehead microphones in accordance with these embodiment have a substantially thin arrangement so as not to be visible to others through the recipient's forehead tissue, but are configured to detect sound signals through the recipient's forehead tissue.

Figure 10A:
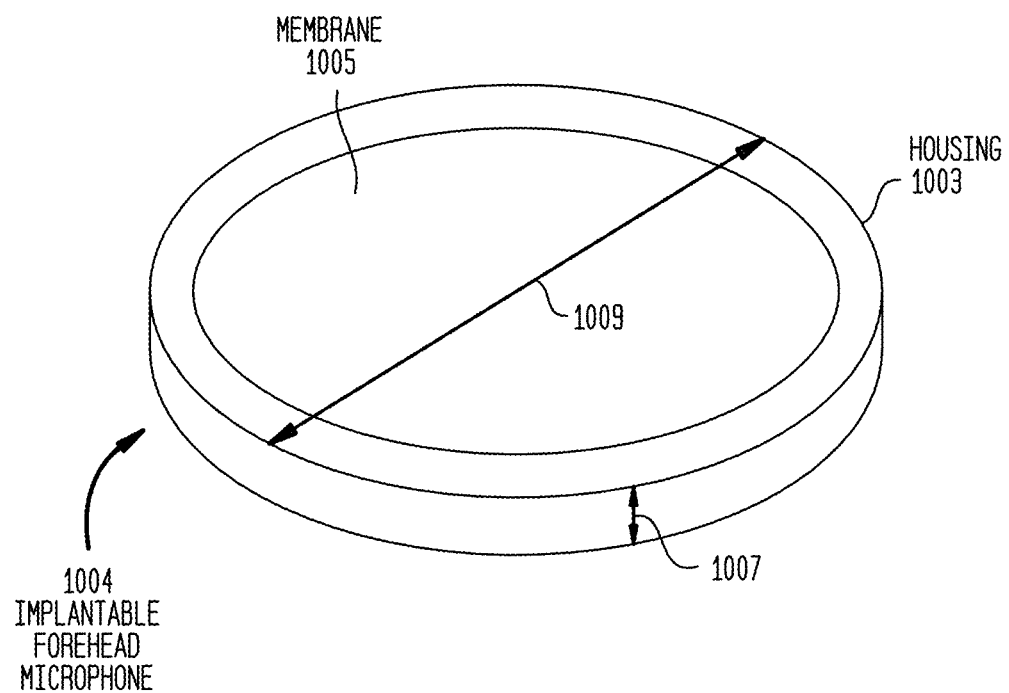
FIG. 10A is a perspective view of an implantable forehead microphone in accordance with embodiments presented herein.
Figure 10B:
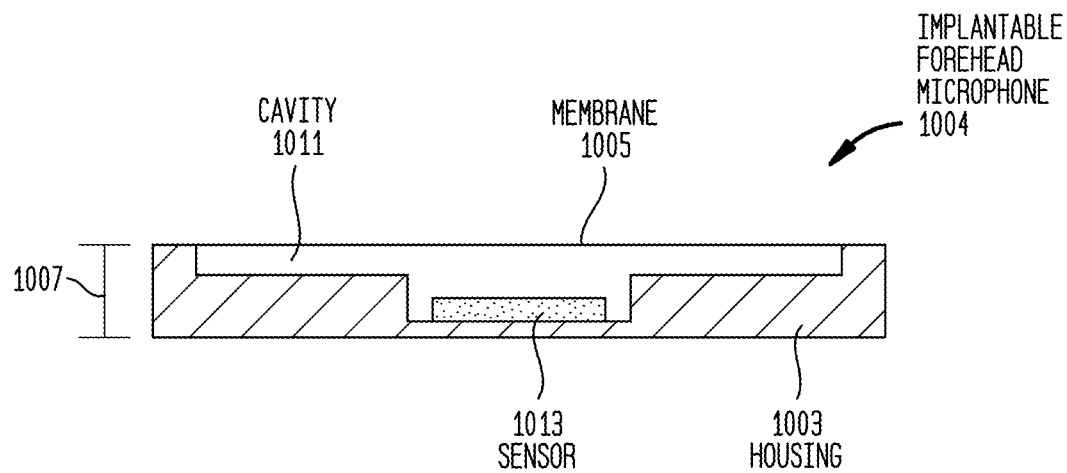
FIG. 10B is a simplified cross-sectional view of the implantable forehead microphone of FIG. 10A.

FIGS. 10A and 10B are perspective and simplified cross-sectional views, respectively, of an implantable forehead microphone 1004 in accordance with embodiments presented herein. As shown in FIG. 10B, the implantable forehead microphone 1004 comprises a housing 1003 that forms a cavity 1011. A membrane 1005 is disposed on the exterior of the housing 1003 so as to seal the cavity 1011. When implanted, the membrane 1005 is adjacent the recipient's forehead tissue and the housing has a general cylindrical shape, although other shapes and arrangements may be used in alternative embodiments. The membrane 1005 may be formed, for example, from titanium.

In operation, the membrane 1005 is configured to vibrate/deflect in response to sound signals that pass through the recipient's forehead tissue. A transducer or sensor 1013 is positioned at a distal end of the cavity 1011 opposing the membrane 1005 as to detect the vibration/deflection of the membrane 1005 and to convert the detected vibration/deflection into an electrical signal representative of the sound signals.

As noted above, implantable forehead microphones in accordance with embodiments presented herein have a substantially thin arrangement. In certain embodiments, the housing 1003 of microphone 1004 has a thickness 1007 of approximately less than 3 millimeters (mm) and a diameter or outer dimension 1009 of between approximately 5 mm and 30 mm.

Figure 11A:
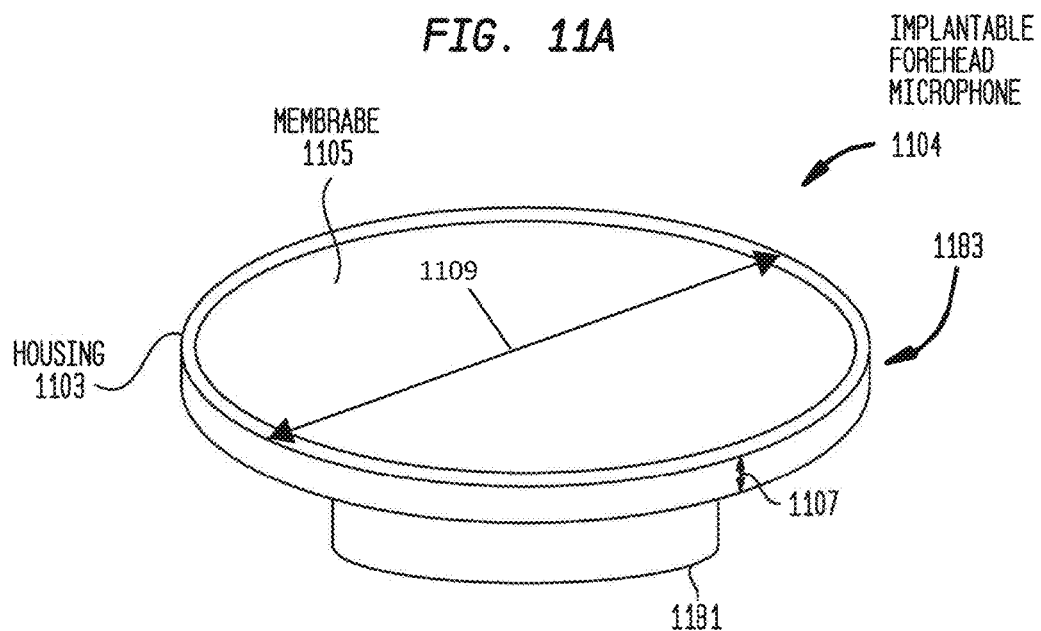
FIG. 11A is a perspective view of another implantable forehead microphone in accordance with embodiments presented herein.
Figure 11B:
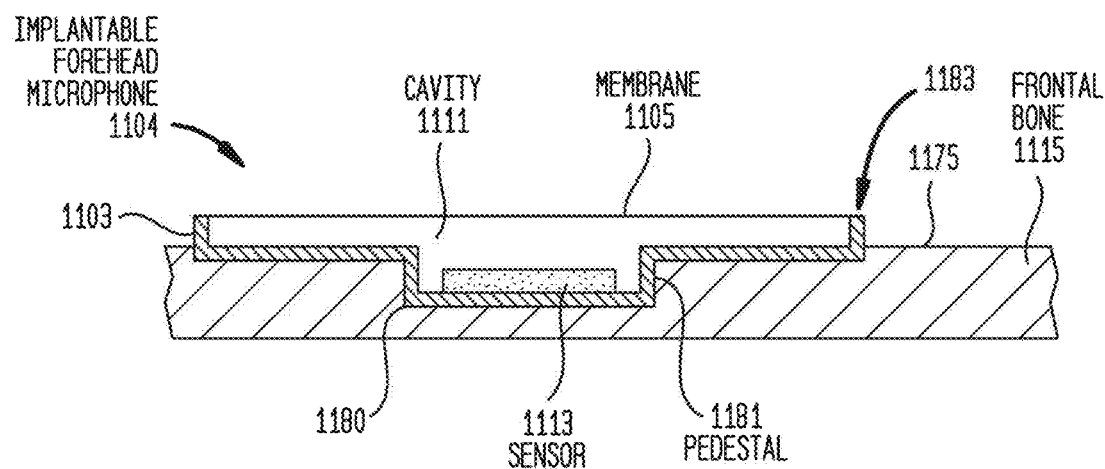
FIG. 11B is a simplified cross-sectional view of the implantable forehead microphone of FIG. 11A.

FIGS. 11A and 11B are perspective and simplified cross-sectional views, respectively, of another implantable forehead microphone 1104 in accordance with embodiments presented herein. The implantable forehead microphone 1104 comprises a housing 1103 that forms a cavity 1111. As shown, the housing 1103 includes a main portion 1183 and an extension or pedestal 1181 that is designed to fit into a surgically-created opening formed in the recipient's frontal bone 1115.

More specifically, FIG. 11B illustrates that the pedestal 1181 of the implantable forehead microphone 1104 is implanted within a surgically-created pocket 1180 formed in the recipient's frontal bone 1115. As shown, the pocket 1180 extends only partially through the recipient's frontal bone 1115 from the outer surface 1175. As such, the main portion 1183 of the of the implantable forehead microphone 1104 is located on the outer surface 1175 of the frontal bone 1115, while the pedestal 1181 extends into the frontal bone. The main portion 1183 is located between the outer surface 1175 and the recipient's forehead tissue (not shown in FIG. 11B).

The implantable forehead microphone 1104 includes a membrane 1105 that is disposed on the exterior of the housing 1103 so as to seal the cavity 1111. When implanted, the membrane 1105 is adjacent the recipient's forehead tissue. In operation, the membrane 1105 is configured to vibrate/deflect in response to sound signals that pass through the recipient's forehead tissue. A sensor 1113 is positioned at a distal end of the cavity 1111 opposing the membrane 1105 as to detect the vibration/deflection of the membrane 1105 and to convert the detected vibration/deflection into an electrical signal representative of the sound signals.

As noted above, implantable forehead microphones in accordance with embodiments presented herein have a substantially thin arrangement. In the specific embodiment of FIGS. 11A and 11B, the pedestal 1181 provides additional space for the sensor 1113 and other components to be located within the recipient's frontal bone 1115. Therefore, the main portion 1183 only includes the membrane 1105 and a portion of the cavity 1111 that is sufficient to allow for the vibration/deflection of the membrane. As a result, the main portion 1183, which is located on the outer surface 1175 of the front bone 1115, may be made extremely thin. For example, the main portion 1183 may have a thickness 1107 of less than 1 mm and a diameter or outer dimension 1109 of between approximately 5 mm and 30 mm.

As noted above, a subcutaneous or implantable forehead microphone is a device implantable in a recipient's forehead region skin so as to receive an acoustic sound signal (sound waves) originating external to the recipient, and convert the acoustic sound signal into electrical signals. Implantable forehead microphones provide good directionality because the microphone is generally forward facing and, as such, are more sensitive to sound from the recipient's front hemisphere, whereas an ear mounted microphone is more sensitive to the recipient's left or right hemisphere. Also as noted above, implantable forehead microphones generally enable a recipient to hear at night (i.e., the forehead typically is not covered by a pillow).

Figure 12:
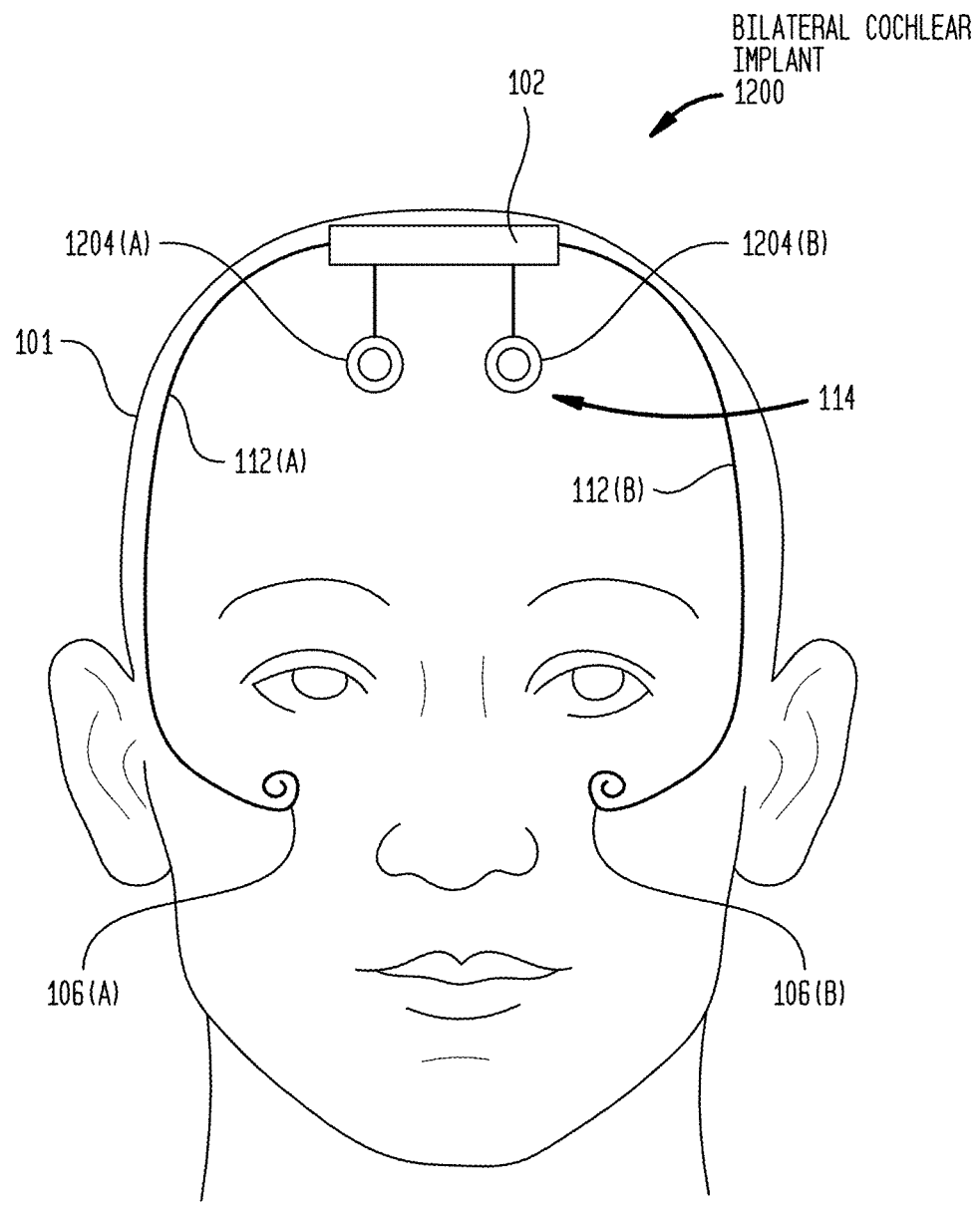
FIG. 12 is a schematic diagram of a bilateral cochlear implant having two implantable forehead microphones in accordance with embodiments presented herein.

Although embodiments have primarily described with reference to the use of one implantable forehead microphone, it is to be appreciated additional implantable forehead microphones or other implantable microphones may be used in embodiments presented herein. For example, FIG. 12 is a schematic diagram of a totally implantable bilateral cochlear implant 1200 that includes two implantable forehead microphones in accordance with embodiments presented herein. The bilateral cochlear implant 1200 of FIG. 12 is substantially similar to bilateral cochlear implant 100 in that it includes the single-body calvaria implant 102 and the bilateral stimulating assemblies 106(A) and 106(B). However, in the embodiment of FIG. 12, the bilateral cochlear implant 1200 includes two (2) implantable forehead microphones 1204(A) and 1204(B) implanted in the recipient's forehead region 114. As shown, the implantable forehead microphones 1204(A) and 1204(B) are laterally spaced from one another so as to enable the bilateral sound processor to perform directional processing, including ambient noise reduction. In certain examples, one of the implantable forehead microphones 1204(A) or 1204(B) may be replaced by a vibration sensor for use in body noise reduction.

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A totally-implantable bilateral hearing prosthesis, comprising:
    first and second stimulation arrangements configured to be implanted at a left and right ear, respectively, of a recipient;
    one or more sound input elements configured to receive sound signals; and
    a single-body calvaria implant electrically connected to the first and second stimulation arrangements, and comprising:
        a hermetically-sealed housing,
        a bilateral sound processor disposed in the housing, and
        a bilateral stimulator unit disposed in the housing,
    wherein the bilateral sound processor and bilateral stimulator unit are configured to convert the sound signals received via the one or more sound input elements into bilateral stimulation signals that are delivered to the recipient via the first and second stimulation arrangements.

2. The bilateral hearing prosthesis of claim 1, wherein the one or more sound input elements include at least one implantable forehead microphone configured to be positioned on the frontal bone of the recipient.

3. The bilateral hearing prosthesis of claim 2, wherein the at least one implantable forehead microphone comprises first and second laterally spaced implantable forehead microphones.

4. The bilateral hearing prosthesis of claim 2, wherein the one or more sound input elements include at least one external sound input element.

5. The bilateral hearing prosthesis of claim 4, wherein the single-body calvaria implant includes a wireless transceiver, and wherein the at least one external sound input element comprises an in-the-ear (ITE) microphone unit that includes a microphone and wireless transmitter for wireless streaming of data to the wireless transceiver in the single-body body calvaria implant.

6. The bilateral hearing prosthesis of claim 1, further comprising:
    a plurality of hermetic electrical connectors that electrically connect at least the first and second stimulation arrangements to the bilateral stimulator unit.

7. The bilateral hearing prosthesis of claim 1, wherein the first and second stimulation arrangements comprise first and second intra-cochlear stimulating assemblies configured to be implanted in the left and right inner ears, respectively, of the recipient.

8. The bilateral hearing prosthesis of claim 1, wherein the single-body calvaria implant includes a rechargeable battery, an implantable radio-frequency (RF) coil, an RF transceiver, and an implantable magnetic component co-located with the RF coil.

9. The bilateral hearing prosthesis of claim 8, wherein the RF coil is disposed inside the housing.

10. A system comprising a recharging unit and the bilateral hearing prosthesis of claim 8, wherein the recharging unit includes an external RF coil and a magnet co-located with the external RF coil configured to align the external RF coil with the implantable RF coil to form a transcutaneous inductive charging link for transfer of power signals from the recharging unit to the single-body calvaria implant.

11. The system of claim 10, wherein the recharging unit is a wireless recharging unit that includes an external rechargeable battery, and wherein the external RF coil is a dual-use coil configured to inductively receive power signals from a charging station for recharging of the external rechargeable battery.

12. A hearing prosthesis method, comprising:
positioning an implantable module in a recipient, wherein the implantable module includes a sound processor and a stimulator unit;
positioning at least one totally-implanted microphone in a recipient's forehead region adjacent to a frontal bone of the recipient's skull;
receiving, with the totally-implanted microphone, sound signals through forehead tissue of the recipient;
converting the sound signals into electrical signals; and
providing the electrical stimulation signals to the sound processor in the implantable module for conversion into stimulation signals for delivery to the recipient.

13. The hearing prosthesis method of claim 12, wherein positioning the at least one totally-implanted microphone in the recipient's forehead region adjacent to a frontal bone of the recipient's skull comprises:
positioning laterally-spaced first and second implantable microphone in the recipient's forehead region.

14. The hearing prosthesis method of claim 12, wherein positioning the implantable module in a recipient comprises:
positioning a single-body implant at a calvaria of the recipient, wherein the single-body implant includes a rechargeable battery, an implantable radio-frequency (RF) coil, an RF transceiver, and an implantable magnetic component co-located with the RF coil.

15. The hearing prosthesis method of claim 14, further comprising:
positioning a recharging unit on the recipient's head, wherein the recharging unit includes an external RF coil and a magnet co-located with the external RF coil configured to align the external RF coil with the implantable RF coil to form a transcutaneous inductive charging link for transfer of power signals from the recharging unit to the single-body implant.

16. The hearing prosthesis method of claim 15, wherein the recharging unit is a wireless recharging unit that includes an external rechargeable battery, and wherein the method further comprises:
inductively receiving, via the external RF coil, power signals from a charging station for recharging of the external rechargeable battery.

17. A totally-implantable bilateral hearing prosthesis, comprising:
at least one implantable microphone configured to be implanted in a head of the recipient and to receive sound signals through tissue of the recipient;
an implantable module including a sound processor and a stimulator unit collectively configured to convert the sound signals into electrical stimulation signals; and
first and second stimulation arrangements each electrically connected to the implantable module and configured to deliver the electrical stimulation signals to left and right ears, respectively, of the recipient.

18. The bilateral hearing prosthesis of claim 17, wherein the implantable module comprises:
a single-body implant positioned at a calvaria of the recipient, wherein the single-body implant includes a rechargeable battery, an implantable radio-frequency (RF) coil, an RF transceiver, and an implantable magnetic component co-located with the RF coil.

19. The bilateral hearing prosthesis of claim 17, wherein the one or more sound input elements include at least one implantable forehead microphone configured to be positioned on the frontal bone of the recipient.

20. The bilateral hearing prosthesis of claim 17, wherein the first and second stimulation arrangements comprise first and second intra-cochlear stimulating assemblies configured to be implanted in the left and right inner ears, respectively, of the recipient.

* * * * *